(12) United States Patent
Chaudhuri

(10) Patent No.: US 8,496,917 B2
(45) Date of Patent: Jul. 30, 2013

(54) COMPOSITIONS AND METHODS FOR IMPROVING SKIN APPEARANCE

(75) Inventor: Ratan K. Chaudhuri, Lincoln Park, NJ (US)

(73) Assignee: Sytheon Ltd, Boonton, NJ (US)

( * ) Notice: Subject to any disclaimer, the term of this patent is extended or adjusted under 35 U.S.C. 154(b) by 149 days.

(21) Appl. No.: 12/938,743

(22) Filed: Nov. 3, 2010

(65) Prior Publication Data

US 2011/0117036 A1    May 19, 2011

Related U.S. Application Data

(60) Provisional application No. 61/260,864, filed on Nov. 13, 2009.

(51) Int. Cl.
| | |
|---|---|
| *A61K 8/49* | (2006.01) |
| *A61K 8/00* | (2006.01) |
| *A61K 31/34* | (2006.01) |
| *C07D 493/02* | (2006.01) |

(52) U.S. Cl.
USPC ............. 424/60; 424/59; 514/470; 549/464

(58) Field of Classification Search
None
See application file for complete search history.

(56) References Cited

U.S. PATENT DOCUMENTS

| 4,297,290 A | 10/1981 | Stockberger |
| RE33,748 E | 11/1991 | Meyborg et al. |
| 5,520,918 A * | 5/1996 | Smith ........................ 424/401 |
| 6,395,810 B1 * | 5/2002 | Luitjes et al. ............... 524/109 |
| 6,693,209 B2 | 2/2004 | Van Es et al. |
| 8,129,549 B2 | 3/2012 | Fuertes et al. |
| 2003/0082129 A1 * | 5/2003 | Buckingham et al. ..... 424/70.12 |
| 2007/0202315 A1 * | 8/2007 | Duffield et al. ............ 428/304.4 |

FOREIGN PATENT DOCUMENTS

| EP | 0065267 A2 | 11/1982 |
| JP | 59-175408 A | 10/1984 |

OTHER PUBLICATIONS

DE3417234, Abstract provided.*

* cited by examiner

*Primary Examiner* — Blessing Fubara
*Assistant Examiner* — Jennifer Berrios
(74) *Attorney, Agent, or Firm* — IP&L Solutions; Edward K Welch, II

(57) ABSTRACT

Skin conditioning compositions comprising a C4 to C30 monoalkyl-, dialkyl, monoalkanoyl- or dialkanoyl-substituted isohexide are found to exhibit a marked effect on skin hydration and barrier function homeostasis thereby improving skin appearances.

18 Claims, No Drawings

COMPOSITIONS AND METHODS FOR IMPROVING SKIN APPEARANCE

This application claims the benefit of U.S. Provisional Patent Application No. 61/260,864 filed Nov. 13, 2009.

FIELD OF THE INVENTION

The present invention relates to the amelioration, reduction and/or reversal of mammalian skin aging, particularly improving hydration of the dermis and epidermis and regulating both epidermal differentiation and lipid synthesis/secretion, which in turn influence permeability barrier homeostasis. Specifically, certain monoalkyl-, dialkyl-, monoalkanoyl- and dialkanoyl-isohexides, also known as the isosorbides, isomannides and isoidides, have now been found to markedly improve and/or maintain skin appearance despite various environmental and/or pathological conditions. It is believed that this is a result of these compounds affecting the expression of certain genes and proteins associated with skin health and appearance.

BACKGROUND OF THE INVENTION

The epidermis of the skin is a stratified squamous epithelium, which plays an important protective role. It manifests this role by building an extensive cytoskeletal architecture, the unique feature of which is the presence of keratin filaments. There are two major pairs of keratins in the epidermis: one pair is expressed in dividing cells and the other expressed in terminally differentiating cells (E Fuchs, Epidermal differentiation and keratin gene expression, J Cell Sci Suppl, 7:197-208; 1993).

For terminal differentiation, epidermal cells move from the basal layer through the spinous layer and the granular layer towards the stratum corneum. During this process, they develop from mitotically active cells into dead, flattened squames. At the various stages of this development, different proteins are expressed. Crosslinking of epidermal proteins eventually leads to the establishment of the cornified envelope, a thick peripheral protein envelope that stabilizes each corneocyte. Additionally, lipids are synthesized in lamellar granules which are subsequently extruded into the extracellular space where they surround the corneocytes and build the lipid envelope. The stratum corneum is an impermeable, insoluble, and highly protective fortress, which keeps microorganisms out and essential bodily fluids in.

The squamous stratified epithelium of the skin is one of the most important barriers of the body, separating it from the surrounding environment and preventing the loss of water and solutes. For decades, the barrier function has mainly been ascribed to the stratum corneum with its corneocytes, cornified envelope and intercellular lipid accumulations: the role of tight junctions (TJs) in the barrier function of epidermis has, in general, been overlooked. However, with recent findings, the role and importance of TJs has come to the forefront. TJs are very complex structures that are formed by transmembrane, plaque and scaffolding proteins. Transmembrane proteins, that is, the family of claudins, occludins and the family of junctional adhesion molecules (JAMs), and scaffolding proteins, such as the zonula occludens (ZO), are important for the formation and regulation of the permeability barrier and for the formation of a molecular fence that separates lipids from apical and basolateral parts of the cell; are contact sites for cell surface receptors, for example, TGF-β-receptor, and molecules of signal transduction pathways; and are involved in the interaction with cells of the immune system, for example, neutrophils. They are often targets for pathogens and their toxins as well as allergens Tight junctions are a dynamic structure with a plurality of distinct, yet somewhat interrelated, functions including permeability (barrier function), polarity (fence function), signaling (cell growth & differentiation), regulation (gene expression & cell proliferation), and tumor suppression. Of these, perhaps the most critical relative to skin aging and the maintenance of skin appearance is its permeability or barrier properties.

TJs form a diffusion barrier that regulates the flux of hydrophilic molecules through the paracellular pathway. Structurally, the TJs form a continuous network of parallel, interconnected intramembrane strands. The TJ strands consist of peripheral and integral membrane proteins that build up morphologically distinguishable strands and connect neighboring cells. Occludin was originally considered important in the formation and sealing of TJs, because the antibody for occludin recognized the strands of TJs. However, it was found that occludin was not essential in the formation of TJ strands, suggesting that it is a regulatory or more of a regulatory protein rather than a structural protein. Whereas only one occludin gene exists, claudin occurs in a multigene family with 24 or more forms. Claudin-1, -2 and -4 have been found to be essential for TJ function in functional analyses. Furthermore, studies of the expression of six different claudin proteins (claudin-1, -2, -3, -4, -5, and -7) in three tissues (liver, kidney, and pancreas) of aging male and female mice and found an age-dependent decrease in the expression of several claudin proteins in all three tissues observed. (T D'Souza, C A Sherman-Baust, S Poosala, J M Mullin and P J Morin, Age-Related Changes of Claudin Expression in Mouse Liver, Kidney, and Pancreas, The Journals of Gerontology Series A: Biological Sciences and Medical Sciences Advance Access published online on Aug. 19, 2009). This suggests another basis for the decrease in tissue barrier function and hence loss of hydration and the manifestation of skin aging in older individuals.

Another structure associated with the TJs is the desmosomes. Desmosomes are adhesive intercellular junctions that attach cell surface adhesion proteins to intracellular keratin filaments (E Delva et al, The Desmosomes, Cold Spring Harbor Perspective in Biology, 2009, 1:a002543). Abnormality in the desmosome-keratin filament complex leads to a breakdown in cell adhesion (fragility) and increase in Trans Epidermal Water Loss (TEWL). Key genes/proteins involved in maintaining desmosome functions include:

Desmogleins & Desmocollins (members of the Cadherin super family) which mediate adhesion at desmosomes; provide structural integrity of the epidermis; and modulate keratinocyte proliferation and differentiation;

Plakoglobin & Plakophillins which recruit intermediate filaments to sites of desmosome assembly and maintain desmosomal integrity Desmoplakin which mediate linkage to the cytoskeleton-pivotal in the development of epidermis; and Cadherin which mediates $Ca^{2+}$-dependent contact between adjacent cells and whose lack of expression causes separation of keratinocytes & weakened desmosomal adhesion;

Water homeostasis of the epidermis is essential for the normal function of the skin and for normal stratum corneum (SC) hydration. It is a determinant of skin appearance, mechanical properties, barrier function, and metabolism. In addition, it is indispensable to maintaining proper water balance of the body. Dehydration of SC is a typical feature of skin aging, especially in photo-aged skin, and of several diseases, for example, eczema, atopic dermatitis, psoriasis, and hereditary ichthyosis. (M Takenouchi, H Suzuki, H Tagami, Hydration characteristics of pathologic stratus corneum-evaluation of bound water, *J Invest Dermatol,* 87 (5):574-576, 1986; P Thune, Evaluation of the hydration and the water-holding capacity in atopic skin and so-called dry skin, *Acta Derm Venerol Suppl,* 144:133-135, 1989; R J Scheuplein, I H Blank, Permeability of the Skin, *Physiol Rev,* 51 (4):702-747, 1971). SC hydration also appears to be directly linked to hyperplasia and inflammation which argues for a biosensor function of water content (Y Ashida, M Ogo, M Denda, Epidermal interleukin-1-alpha generation is amplified at low humidity: implications for the pathogenesis of inflammatory dermatoses *Br J Dermatol,* 144 (2):238-243, 2001; M Denda, J Sato, T. Tsuchiya, Low humidity stimulates DNA synthesis and amplifies the hyperproliferative dermatoses, *J Invest Dermatol,* 111 (5): 873-878, 1998).

In order to maintain and improve skin hydration, one needs to address both water homeostasis and functions related to structural barrier mechanisms, such as, tight junction, desmosome and epidermal differentiation, thereby improving skin health and appearance.

Water homeostasis depends on several factors, for example, the supply of water from the body, water diffusion from the viable layers of the epidermis, trans-epidermal water loss (TEWL), and water-holding capacity of stratum corneum. Supply of water from the body depends on its water balance and putatively on blood circulation. Water diffusion through the epidermis depends on transcellular as well as paracellular pathways along osmotic gradients. Transcellular diffusion is performed through pores, i.e., proteins that act as pores, in the plasma membrane which are called aquaglyceroporins, a subgroup of the aquaporin (AQP) family, as well as directly through plasma membranes. Paracellular diffusion might be controlled by tight junctions (TJ) and TJ proteins. TEWL depends on the barrier function of the skin, which is influenced by, among others, TJ proteins; on the environmental conditions encountered, for example, high and low humidity and temperature; and on the water supply present. SC water-holding capacity is thought to depend on SC structure and composition, particularly the content of natural moisturizing factors and humectants like glycerol.

Aquaglyceroporins are best known and responsible for transporting both water and small neutral solutes, such as glycerol. One of the key aquaglyceroporins is water channel aquaporin 3 (AQP3). AQP3 is the most abundant AQP in human epidermis and is responsible for hydration in human skin epidermis. AQP3 was first cloned from rat kidney (S Sasaki, K Fushimi, H Saito, F Saito, S Uchida, K Ishibashi et al, Cloning, characterization, and chromosomal mapping of human aquaporin of collecting duct, *J Clin Invest,* 93:1250-1256, 1994) and subsequently found in red blood cells (N Roudier, J M Verbavatz, C Maurel, P Ripoche, F Tacnet, Evidence for the presence of aquaporin-3 in human red blood cells, *J Biol Chem,* 273:8407-8412, 1998), chondrocytes (A Mobasheri, E Trujillo, S Bell, S D Carter, P D Clegg, P Martin-Vasallo et al., Aquaporin water channels AQP1 and AQP3, are expressed in equine articular chondrocytes, *Vet J,* 168:143-150, 2004), and in epithelial cells from the urinary, digestive, and respiratory systems (A Frigeri, M A Gropper, F Umenishi, M Kawashima, D Brown, A Verkman A, Localization of MIWC and GLIP water channel homologs in neuromuscular, epithelial and glandular tissues, *J Cell Sci,* 108: 2993-3002, 1995). In skin, AQP3 is constitutively expressed by epidermal keratinocytes (R Sougrat, M Morand, C Gondran, P Barre, R Gobin, F Bonte et al., Functional expression of AQP3 in human skin epidermis and reconstructed epidermis, *J Invest Dermatol,* 118:678-685, 2002). AQP3-deficient mice suffer from reduced water and glycerol permeabilities and decreased water holding capacity of the stratum corneum, demonstrating a pivotal role of this channel in the maintenance of skin hydration (T Ma, M Hara, R Sougrat, J M Verbavatz, A S Verkman, Impaired stratum corneum hydration in mice lacking epidermal water channel aquaporin-3, *J Biol Chem,* 277:17147-17153, 2002). AQP3-deficient mice also show delayed barrier recovery after tape-stripping disruption and delayed wound healing (M Hara, T Ma, A S Verkman, Selectively reduced glycerol in skin of aquaporin-3-deficient mice may account for impaired skin hydration, elasticity, and barrier recovery, *J Biol Chem,* 277:46616-46621, 2002), suggesting a possible role of AQP3 in the regulation of keratinocyte differentiation and proliferation.

One of the major characteristics of human skin photoaging induced by ultraviolet (UV) radiation is the dehydration of the skin (C Cao, S Wan, Q Jiang, A Amaral, S Lu, G Hu, Z Bi, N Kouttab, W Chu, Y Wan, *J Cell Physiol,* 215 (2):506-516, 2008). Water movement across plasma membrane occurs via diffusion through lipid bilayer and via aquaporins (AQPs). It has been shown that UV induces aquaporin-3 (AQP3) down-regulation in human skin keratinocytes.

AQP3 may also play a role in sebaceous gland physiology, as it is expressed in the sebaceous gland (A Frigeri, M A Cropper, F Umenishi, M Kawashima, D Brown and A S Verkman, Localization of MIWC and CLIP water channel homologs in neuromuscular, epithelial and glandular tissues. *J Cell Sci* 108:2993-3002, 1995). Analysis of sebaceous gland-deficient mice suggested that sebaceous gland-derived glycerol is an important contributor to SC hydration (J W Fluhr, M Mao-Qiang, B E Brown, P W Wertz, D Crumrine, J P Sundberg, K R Feingold and P M Elias, Glycerol regulates stratum corneum hydration in sebaceous gland deficient (asebia) mice, *J Invest Dermatol* 120:728-737, 2003). Another group reported co-localization of AQP3 with phospholipase D2 in keratinocytes and suggested that phosphatidylglycerol synthesis might be facilitated by AQP3-mediated glycerol transport and phospholipase D2 action (X Zheng, and W B Bollag, Aquaporin 3 colocates with phospholipase D2 in caveolin-rich membrane microdomains and is down-regulated upon keratinocyte differentiation, *J Invest Dermatol* 121:1487-1495, 2003). Phospholipids including phosphatidylglycerol are involved in epidermal lipid biosynthesis, which are important in maintaining lamellar lipid structure and SC barrier function.

In summary, AQP3 has been shown to play an important role in epidermal glycerol transport and steady-state accumulation of glycerol in epidermis and SC providing a rational scientific basis for the longstanding practice of including glycerol in cosmetic and skin medicinal preparations. Thus, activation/up-regulation of AQP3 should improve skin hydration, barrier function and skin appearance, possibly reducing skin sagging and wrinkling.

Retinoids are important regulators of several biological processes such as embryogenesis, reproduction, differentiation, proliferation, and apoptosis. By regulating keratinocyte proliferation and differentiation, retinoids increase stratum granulosum thickness and are widely used in cosmetics for the treatment of skin aging. Retinoic acid has been shown recently to stimulate AQP3 gene and protein expression in normal human epidermal keratinocytes (NHEK) as well as in skin explants and to increase glycerol transport capacity, indicating that stimulation of AQP3 expression was accompanied by an enhancement of biological activity. Over expression of functional AQP3 may increase skin glycerol content, which in turn may be a key messenger of keratinocyte proliferation and early differentiation processes. The recent finding that retinoids increase AQP3 expression and stimulate glycerol transport further confirms that, beyond its humectant properties, glycerol may actually play a biological role in epidermal maturation.

However, there are contradictory viewpoints which suggest that over-expression of AQP3, at least in part, accounts for skin dryness. Phenotypical studies in AQP3 null mice indicate that AQP3 plays an important role in epidermal glycerol and water transport and that up-regulation of AQP3 leads to more water movement from dermis to epidermis. In AQP3-deficient mice, skin barrier recovery and wound healing is significantly delayed, while up-regulation of AQP3 facilitates epidermal cell migration during wound healing. However, hyper-expression of AQP3 is also associated with the increase of TEWL. A decrease in the water-holding capacity of the stratum corneum combined with an increase in water transport to the stratum corneum may lead to more water loss and skin dryness. This is consistent with the finding that increased AQP3 expression is found in the epidermis of patients with atopic eczema (AE), a diSease characterized by dry skin, in contrast with that of healthy skin. Patients with AE show defective skin barrier function and reduced water-holding capacity in stratum corneum which are believed to contribute to increased water loss and dry skin in AE. These findings demonstrate that increased expression of AQP3 may lead to increased water loss in AE. However, improving barrier function in AE may resolve excess water loss and dryness.

All-trans retinoic acid (atRA) has been shown to up-regulate the expression of AQP3. (G Bellemère, Von Stetten and T Oddos, Retinoic Acid Increases Aquaporin 3 Expression in Normal Human Skin, J Invest Dermatol, 128:542-548, 2008.) Nicotinamide has been shown to decrease the expression of AQP3 and water permeability induced by all-trans retinoic acid (atRA) in a concentration-dependent manner. Specifically, nicotinamide attenuates atRA-induced AQP3 hyperexpression. These finding may further explain why atRA therapy induces skin dryness when it is used topically and suggest that nicotinamide may be used as a moisturizer by down-regulating the expression of AQP3 in keratinocytes. Earlier studies have shown that topical nicotinamide improves skin barrier function, and nicotinamide cream is an effective moisturizer on atopic dry skin and may be used as an auxiliary medicine to treat atopic dermatitis. For example, the administration with myristyl nicotinate for one month has been found to reduce skin TEWL and provide additional barrier protection and tolerability of retinoic acid without interfering with improving efficacy.

Thus, AQPs appear to be key protein targets to improve the resistance and quality of the skin surface as well as to improve aging and sun exposure-induced dryness as shown by their roles in (1) hydrating the living layers of the epidermis where the keratinocyte differentiation takes place and (2) improving barrier formation, function and recovery. Indeed, considerable effort have been undertaken to develop techniques and compositions for improving skin appearance by stimulating aquaporins. For example, Breitenbach et. al. (US 2009/1030223; WO 2007/124991) describe a method of stimulating aquaporin expression in skin by contacting the skin with at least one of a glyceryl glycoside and a derivative thereof in an amount which is effective for stimulating aquaporin expression in the skin. Sene et. al. (US 2009/0036402) describe a composition for activating at least one of AQP-3, filaggrin or transglutaminase in the skin of an animal, comprising at least one compound from Centella Asiatica selected from the group consisting of madecassoside, terminoloside, asiaticoside, madecassic acid, asiatic acid and mixtures thereof. Xie et. al. (US 2007/0009474) describe personal care compositions comprising from about 0.05% to about 5% of at least one aquaporin-stimulating compound selected from the group consisting of xanthine, caffeine; 2-amino-6-methylmercaptopurine; 1-methyl xanthine; 2-aminopurine; theophylline; theobromine; adenine; adenosine; kinetin; p-chlorophenoxyacetic acid; 2,4-dichlorophenoxyacetic acid; indole-3-butyric acid; indole-3-acetic acid methyl ester; beta-naphthoxyacetic acid; 2,3,5-triiodobenzoic acid; adenine hemisulfate; n-benzyl-9-(2-tetrahydropyranyl)adenine; 1,3-diphenylurea; 1-phenyl-3-(1,2,3-thiadiazol-5-yl)urea; zeatin; indole-3-acetic acid; 6-benzylaminopurine; alpha-napthaleneacetic acid; 6-2-furoylaminopurine; green tea extract; white tea extract; menthol; tea tree oil; ginsenoside-RB1; ginsenoside-RB3; ginsenoside-RC; ginsenoside-RD; ginsenoside-RE; ginsenoside-RG1; ginseng root extract; ginseng flower extract; pomegranate extract, extracts from Ajuga turkestanica; extracts from viola tricolor and combinations thereof; an additional ingredient selected from the group consisting of niacinamide, glycerin and mixtures thereof, and a dermatologically-acceptable carrier. Thiem et. al. (EP0770378) describes cosmetic or pharmaceutical preparations comprising hexosylglycerides and/or (hexosyl)hexosylglycerides as well as the use of glycosyl glycerides as agents which enhance skin moistness. Such studies are not limited to the patent literature, as numerous technical articles have been presented on the subject as well including: M Dumas, C Gondran, P Barré, R Sougrat, J M Verbavatz, C Heusèle, S Schnébert, F Bonté, Effect of an Ajuga turkestanica extract on aquaporin 3 expression, water flux, differentiation and barrier parameters of the human epidermis, Eur J Dermatol, 12 (6):XXV-XXVI, 2002 and M Zelenina, S Tritto, A A Bondar, S Zelenin, A Aperia, Copper inhibits the water and glycerol permeability of aquaporin-3, J Biol Chem, 279 (50):51939-51943, 2004.

Another factor key to TEWL and the integrity of TJs are the zonula occludens. Zonula occluden (ZO) proteins, comprising ZO-1, -2, and -3, are peripheral proteins localizing at junctional sites. ZO proteins are scaffolding proteins recruiting various types of proteins to the cytoplasmic surface of the junction, thereby contributing to the so called "junctional plaque". ZO proteins have originally been described to localize specifically to tight junctions (TJs) (*zonulae occludentes*) [B. R. Stevenson, J. D. Siliciano, and M. S. Mooseker, "Identification of ZO-1: a high molecular weight polypeptide associated with the tight junction (Zonula Occludens) in a variety of epithelia," *Journal of Cell Biology*, vol. 103, no. 3, pp. 755-766, 1986.]. However, this notion was quickly reevaluated, since these proteins were found to associate with the cadherin-based adherens junctions (AJs) in cells lacking TJs [A. G. Howarth, M. R. Hughes, and B. R. Stevenson, "Detection of the tight junction-associated protein ZO-1 in astrocytes and other nonepithelial cell types," *American Journal of Physiology*, vol. 262, no. 2, pp. C461-C469, 1992].

Moreover, ZO proteins also associate with gap junctions (GJs) by directly interacting with connexins [H. Bauer, J Zweimueller-Mayer, P. Steinbacher, A. Lametschwandtner, and H. C. Bauer, The Dual Role of Zonula Occludens (ZO) Proteins, J Biomed and Biotech, vol. 2010, Article ID 402593, 11 pages, 2010. doi:10.1155/2010/402593], which points towards a general role of ZO proteins in intercellular adhesion and communication. The most prominent function of ZO proteins at the junctional site is the regulation of claudin polymerization in epithelial cells, which was demonstrated by use of a reverse genetic approach [K. Umeda, J. Ikenouchi, S. Katahira-Tayama, et al., "ZO-1 and ZO-2 independently determine where claudins are polymerized in tight-junction strand formation," *Cell*, vol. 126, no. 4, pp. 741-754, 2006].

In recent years, intriguing evidence has accumulated suggesting that ZO proteins not only exert functions related to structural barrier mechanisms but are also involved in signal transduction and transcriptional modulation [H. Bauer, J Zweimueller-Mayer, P. Steinbacher, A. Lametschwandtner, and H. C. Bauer, The Dual Role of Zonula Occludens (ZO) Proteins, J Biomed and Biotech, vol. 2010, Article ID 402593, 11 pages, 2010. doi:10.1155/2010/402593].

Despite these findings and the advances made, there is still a definite need for skin care/treatment compositions that are more effective and more forgiving; especially those that are able to improve skin health and appearances. However, in contrast to early efforts, a more fundamental and comprehensive approach is needed for improving skin health and appearances that is based on the biology of the skin. As noted above, decline of skin health and appearance is a natural phenomenon that occurs over time and is not just a result of wear and tear, but is also the consequence of a continually active genetic program that might be up- or down-regulated resulting in detrimental effects on skin. Thus, from a biological standpoint, an effective strategy for improving the health and appearance of skin must include ingredient(s) that provide(s) hydration of the dermis and epidermis and that regulate(s) both epidermal differentiation and lipid synthesis/secretion, which in turn influence permeability barrier homeostasis. Retinoids, while effective, have poor stability and at high levels, especially on a continual basis, results in other adverse consequences including skin sensitization and irritation. Glycerol is effective, but it is tacky and requires high level use. Additionally, glycerol does not give aesthetically pleasing formulations due to tackiness. Glycerylglycosides are not very stable, therefore difficult to formulate and the formulated products have shorter shelf-life.

Plant extracts have found great utility in skin care products; however, their use is not a simple matter. Plant extracts are by nature very complex having numerous constituents in varying concentrations. Identification and selection of the proper plant is critical, even the type of plant, e.g. chemo-, pheno-, and geno-type, which will have a marked influence on the active ingredients. Similarly, the portion of the plant to be used in the extraction process is also important as there are marked differences in the nature and abundance of the chemical constituents in the roots, leaves, bark, and other parts of the plants. Harvesting of the plants also influences the chemical constituents and their concentrations as once harvested certain chemicals may degrade or become more sensitive to degradation by environmental factors. All of these need to be considered and accounted for in the use of plant extracts, particularly for ensuring that the extracts will have the appropriate concentrations and ratios necessary to elicit the desired skin care benefits. The key to getting consistent and predictable results is to have standardized plant extracts, which is seldom the case in commercially available material.

Thus, in light of the foregoing discussion, there continues to be a need for compounds that are capable of stimulating the aquaporin membrane proteins, especially ones that will increase the expression of AQP-3, so as to improve skin hydration and thereby minimize the visual signs of dry or photo-damaged skin, enhancing skin moisturization, appearance, tone, texture and firmness.

Additionally, there continues to be a need for compounds that are capable of stimulating key genes/proteins associated with the tight junctions, desmosomes, and epidermal differentiation for maintaining and/or improving barrier formation, function and recovery in mammalian skin.

SUMMARY OF THE INVENTION

In accordance with the present disclosure there are provided novel isohexide compounds having the formulae A and B:

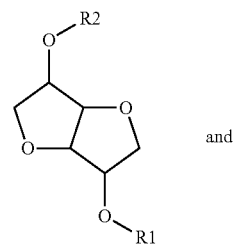

and

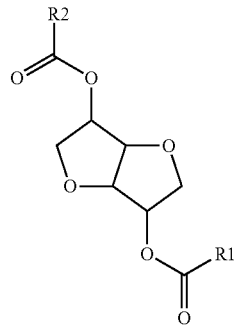

wherein $R_1$ and $R_2$, which may be the same or different, are independently selected from C4 to C10, preferably C6-C8, saturated or unsaturated n-alkyl groups, C5 to C10, preferably C6-C9 branched, saturated or unsaturated alkyl groups; provided that when $R_1$ and $R_2$ are different, one of $R_1$ or $R_2$ may also be hydrogen or a straight chain or branched; saturated or unsaturated alkyl group of from 1 to 3 carbon atoms, In accordance with a second aspect of the present disclosure, there are provided advanced skin care products which ameliorate, reduce and reverse the effects and/or manifestation of skin aging, particularly through improved hydration of the dermis and epidermis and barrier functions and formation. Specifically, it has now been found that topical application of an effective amount of at least one monoalkyl-, dialkyl-, monoalkanoyl- or dialkanoyl-isohexide having the general formula (I) or (II):

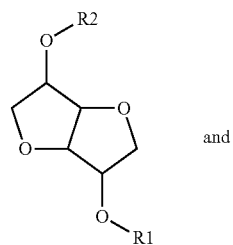

and

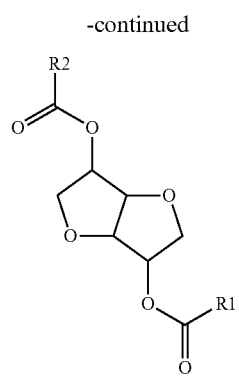

wherein $R_1$ and $R_2$, which may be the same or different, are independently selected from straight chain or branched; saturated or unsaturated alkyl groups having from 4 to 30 carbon atoms, preferably from 6 to 22 carbon atoms, most preferably from 8 to 18 carbon, said carbon number including the carbonyl carbon atom in the case of structure (II), provided that when $R_1$ and $R_2$ are different, one of $R_1$ or $R_2$ may also be hydrogen or a straight chain or branched; saturated or unsaturated alkyl group of from 1 to 4, preferably 1 to 3, carbon atoms, or a composition based upon or containing the same, to the skin results in a marked improvement in skin hydration, barrier function, appearance and health.

In accordance with another aspect of the present disclosure, there are provided pharmaceutical and/or health and beauty compositions, again based upon or containing an effective amount of at least on monoalkyl- dialkyl-, monoalkanoy-l or dialkanoyl-isohexide according to formulae (I) and (II) above that are capable of gene manipulation, which gene manipulation is manifested in an up-regulation of certain genes and, consequently, the increase of certain proteins associated with skin conditioning and maintenance as well as other important biological functions and processes in the human body for overall improved health and conditioning.

In yet another embodiment of the present invention, there is provided a method of ameliorating, reducing and/or reversing the effects or manifestation of skin aging of mammalian skin by applying to the skin an effective amount of at least on monoalkyl- dialkyl-, monoalkanoyl- or dialkanoyl-isohexide according to formulae (I) and (II) above.

The compounds according to formulae (I) and/or (II) may be applied as is, if in liquid form, or in a suitable carrier, particularly a dermatologically acceptable carrier or formulation. Most preferably, these compounds are formulated as part of a skin care product having other active ingredients for skin care and/or conditioning.

DETAILED DESCRIPTION OF THE INVENTION

The present invention is based upon the unexpected finding that certain, high monoalkyl and dialkyl isohexides have a marked effect in ameliorating, reducing and/or reversing the effects and/or manifestation of skin aging. In particular, it has now been found that certain higher carbon number monoalkyl-, dialkyl-, monoalkanoyl- and dialkanoyl-isohexides, also known as the alkyl- and alkanoyl-dianhydrohexitols, such as the monoalkyl-dialkyl-, monoalkanoyl- and dialkanoyl-isosorbides, isomannides and isoidides, are effective in retarding and/or improving skin condition and health. While not intending to be bound by theory or mechanisms, it is believed that these compounds are capable of up-regulating key genes/proteins, such as, Aquaporin 3, Claudin 4, ZO-1, ZO-2 and JAM-1 as well as desmosome and epidermal differentiation genes/proteins thereby providing many of the desired attributes that are required for normal epidermal permeability barrier function, management of water content, skin elasticity and barrier function recovery, factors which enable and manifest improved skin health and appearance.

Dianhydrohexitols are well documented by-products of the starch industry obtained by dehydration of D-hexitols, which are made by a simple reduction of hexose sugars. About 650,000 tons of dianhydrohexitols are produced annually worldwide. These chiral biomass-derived products exist as three main isomers (isosorbide (II), isomannide (III), and isoidide (IV)), depending on the configuration of the two hydroxyl functions (derived from D-glucose, D-mannose, and L-fructose, respectively). Isosorbide, which is produced from glucose via sorbitol, is the most widely available dianhydrohexitol.

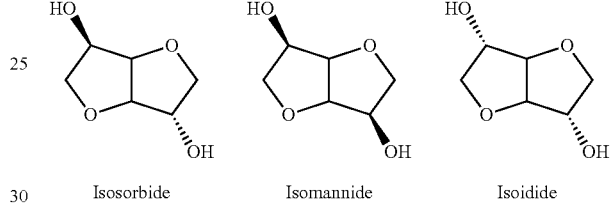

Isosorbide     Isomannide     Isoidide

These three compounds, as well as the lower ($C_1$-$C_4$) mono- and di-alkyl ethers thereof, and the mono and di-nitrates thereof, are well known and already used in various medical, pharmaceutical and health and beauty applications. The unsubstituted and lower alkyl substituted isohexides are very soluble in water and biologically harmless. The lower alkyl ethers and the unsubstituted compounds have been used as carriers in a number of skin care products to aid in the transport of other active ingredients through the skin membrane. The lower alkyl ethers have also found utility in dentifrices, aiding in the removal of plaque due to their osmotic properties. Isosorbide dinitrate and isosorbide mononitrate have been used to treat angina pectoris. Like other nitric oxide donors, these drugs lower portal pressure by vasodilation and decreasing cardiac output.

Surprisingly, it has now been found that monoalkyl-, dialkyl-, monoalkanoyl- or dialkanoyl-isohexide having the general formula (I) or (II):

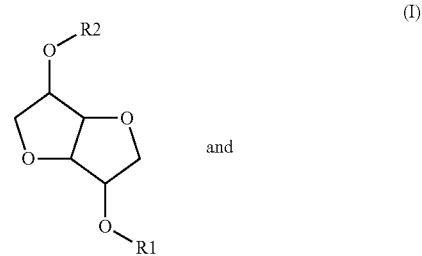

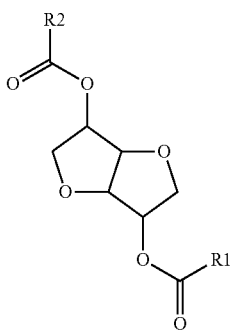

(II)

wherein $R_1$ and $R_2$, which may be the same or different, are independently selected from straight chain or branched; saturated or unsaturated alkyl groups having from 4 to 30 carbon atoms, preferably from 6 to 22 carbon atoms, most preferably from 8 to 18 carbon, said carbon number including the carbonyl carbon atom in the case of structure (II), provided that when $R_1$ and $R_2$ are different, one of $R_1$ or $R_2$ may also be hydrogen or a straight chain or branched; saturated or unsaturated alkyl group of from 1 to 4, preferably 1 to 3 carbon atoms, are extremely effective bioactive compounds, capable of manipulating genes and/or of markedly enhancing or impacting skin appearance and health. It is to be appreciated that in the above formulae, the structural orientation of the —$OR_1$ and —$OR_2$ groups in the case of formula (I) and the —$OC(O)R_1$ and —$OC(O)R_2$ in the case of formula (II) may be in an endo orientation (an isomannide), an exo orientation (an isoidide) or one may be endo and the other exo (an isosorbide). Owing to their structure, the isomannide and isoidide compounds are both symmetrical molecules; whereas, because isosorbide has one endo and one exo group, mono-acylation gives rise to two different non-equivalent ester products, namely a 2-ester or a 5-ester. Generally speaking, these compounds have the characteristics of bis secondary alcohols attached to two cis-fused tetrahydrofuran rings and as such possess the properties of a diol and an ether or ester, as appropriate.

The monoalkyl- and dialkyl-isohexides according to the present invention may be formed by any of the known methods for the alkyl substitution of the isohexides or by modified versions of those methods, as will be apparent to those skilled in the art having the benefit of this disclosure. The most convenient method for their production is by the Williamson ether synthesis technique and modifications thereof wherein a dianhydrohexitol is reacted with an alkyl halide or a sulfate, or a mixture of alkyl halides or sulfates in strong alkali followed by conventional purification and distillation techniques. This alkylation reaction may be under various conditions including in an appropriate solvent, like p-toluene, using KOH as a base either under microwave irradiation or conventional heating. Alternatively, they may be prepared by performing the alkylation reaction with dialkyl carbonates at elevated temperatures and pressures in the presence of a base catalyst.

Suitable methods are described in Kruse et. al, (U.S. Pat. No. 4,435,586); Hillard et. al. (U.S. Pat. No. 4,322,359); Lynch (U.S. Pat. No. 4,627,976); Greenshields (U.S. Pat. No. 4,770,871); Maurer et. al. (U.S. Pat. No. 4,659,846); Soltzberg (U.S. Pat. No. 2,234,200); Brown (U.S. Pat. No. 2,420,519); Chatti et. al. (Cation and Leaving Group Effects in Isosorbide Alkylation Under Microwave in Phase Transfer Catalysis, Tetrahedon 57, 2001, pages 4365-4370); Smith et. al. (Canadian J. Chemistry, 47, 1969, pages 2015-2019); Benedict et. al. (Synthesis, June 1979, pages 428-429); Johnstone et. al. (Tetrahedron, 35, (1979), pages 2169-2172) and Freedman et. al. (Tetrahedron 38, 1975, pages 3251-3254), all of which are hereby incorporated herein by reference in their entirety.

Exemplary alkyl isohexides suitable for use in the practice of the present invention include the dibutyl isosorbide, dibutyl isomannide, dibutyl isoidide, dihexyl isosorbide, dihexyl isomannide, dihexyl isoidide, dioctyl isosorbide, dioctyl isomannide, dioctyl isoidide, butyl isosorbide, butyl isomannide, butyl isoidide, hexyl isosorbide, hexyl isomannide, hexyl isoidide, di-isobutyl isosorbide, di-isobutyl isomannide, di-isobutyl isoidide, methyl octyl isosorbide, methyl octyl isomannide, methyl octyl isoidide, distearyl isosorbide, distearyl isomannide, distearyl isoidide, and the like, as well as mixtures of any two or more of the foregoing.

Similarly, the monoalkanoyl- and dialkanoyl-isohexides according to the present invention may be formed by any of the known methods for the esterification of the isohexides or by modified versions of those methods, as will be apparent to those skilled in the art having the benefit of this disclosure. For example, they may be prepared by nucleophilic acyl substitution where the carbonyl compound is used as an electrophile and is attacked by a nucleophilic alcohol, such as, isohexides in the present invention. Alternatively, one may employ a carboxylate anion as a nucleophile that displaces a halide ion in an SN2 reaction: essentially, esterification by alkylation reverses the roles of "classic" carbonyl chemistry.

Suitable methods are described in, e.g., P. Stoss and R. Hemmer, "1,4:3,6-Dianhydrohexitols", in *Advances in Carbohydrate Chemistry and Biochemistry*, Vol. 49, pp. 93-173 (1991), Z. Cekovic and Z. Tokic, Synthesis, pp. 610-612 (1989); Courtalds Ltd. NL 6,405,497 (1962) and Chem. Abstr., 69 (1968) 67,666, all of which are hereby incorporated herein by reference in their entirety.

Exemplary alkanoyl isohexides suitable for use in the practice of the present invention include the dibutanoyl isosorbide, dibutanoyl isomannide, dibutanoyl isoidide, dihexanoyl isosorbide, dihexanoyl isomannide, dihexanoyl isoidide, dioctanoyl isosorbide, dioctanoyl isomannide, dioctanoyl isoidide, butanoyl isosorbide, butanoyl isomannide, butanoyl isoidide, hexanoyl isosorbide, hexanoyl isomannide, hexanoyl isoidide, di-isobutanoyl isosorbide, di-isobutanyl isomannide, di-isobutanoyl isoidide, methyl octanoyl isosorbide, methyl octanoyl isomannide, methyl octanoyl isoidide, distearoyl isosorbide, distearoyl isomannide, distearoyl isoidide, and the like, as well as mixtures of any two or more of the foregoing.

Typically, the resultant alkyl and alkanoyl isohexides according to these processes will comprise a mixture of isohexides. For example, preparations of dioctanoyl isosorbide (DOI) are likely to contain dioctanoyl isomannide and dioctanoyl isoidide as well as small amounts of the monooctanoyl equivalents. One can isolate or purify the desired alkanoyl isohexide by various purification and distillation techniques known to those skilled in the art. Even so, it is to be realized that essentially pure product are likely to have a small percentage, perhaps 1-2% by weight of each of the other di-substituted isomers as well as 1-2% by weight of the mono-substituted equivalents. A commercial alkanoyl isohexide that is suitable for use in the practice of the present invention is that DOI sold under the trademark Synovea® DOI by Sytheon Ltd. of Boonton, N.J.

As indicated, the alkyl and alkanoyl isohexides may be used in their purified forms or as the isomer mixtures. Alternatively, combinations of purified and/or isomer mixtures of different monoalkyl and/or dialkyl isohexides may be used, combinations of purified and/or isomer mixtures of monoalkanoyl and/or dialkanoyl isohexides may be used as was as mixtures of purified and/or isomer mixtures of both alkyl and alkanoyl isohexides may be used. Most preferably, the isohexides are the monoalkanoyl and/or dialkanoyl isohexides. For simplicity, of discussion and to avoid repetitiveness, henceforth the term alkanoyl isohexides shall be deemed to refer, in general, to the monoalkyl-, dialkyl-, monoalkanoyl- and dialkanoyl-isohexides of formulae (I) and (II) above, collectively. Where it is stated that certain properties and/or functions have been found, it means that at least one member of the foregoing class has been found to show or manifest the specified property or characteristic unless otherwise indicated: though it is believed that the properties and characteristics are common to each class member.

The alkanoyl isohexide compounds and/or mixtures thereof, many of which are believed to be novel, may be used as is or may be formulated with an appropriate carrier or solvent. Preferably, the alkanoyl isohexides are formulated into or combined with a dermatologically acceptable carrier. Most preferably, the alkanoyl isohexide comprises a component of a skin care formulation or product having multiple active components for protecting and/or rejuvenating skin. For example, there are provided compositions for improving skin health and appearance wherein the performance of glycerol or other moisturizers are synergistically enhanced by their combination with one or more alkanoyl isohexide compounds according to the present disclosure. It has also been found that the combination of the alkanoyl isohexide compounds according to the present disclosure with one or more anti-aging actives, especially the meroterpenes, most especially bakuchiol, leads to further improvement in skin health and appearance. This improvement is typically of a marked nature owing to a synergy between the two active components.

In addition to the manifestation of physical improvement in skin appearance and health, the alkanoyl isohexides have also been found to manifest a gene modulation effect. The Gene Ontology analysis shows two types of skin-relevant responses elicited by the alkanoyl isohexides of the present invention. For example, Dioctanoyl Isosorbide (DOI) has demonstrated an overall stimulatory effect on epidermis morphogenesis, through the stimulation of proliferation, migration and differentiation of keratinocytes, accompanied by an increase in angiogenesis. It is interesting to note that this epidermis-stimulatory effect has been observed against a generally conservative background of suppressed gene expression and signal transduction. This data points to the specificity of the stimulatory effect of DOI towards the skin tissue, while maintaining the overall systemic homeostasis. Additionally, exposure to DOI resulted in an activation of some selective components of the immune response, without translation into a chronic inflammatory response. Finally, DOI has shown effects on the genes commonly considered important for improving hydration of the dermis and epidermis, regulating both epidermal differentiation and lipid synthesis/secretion, which in turn influence permeability barrier homeostasis.

The compositions for improving or maintaining skin health and appearance according to the present invention will typically comprise one or more of the specified alkanoyl-isohexides, oftentimes a combination of alkanoyl isohexides, in an amount of from about 0.01 to about 100 wt %, preferably from about 0.5 to about 30 wt %, more preferably from about 0.5 to about 20 wt %, most preferably from about 1.0 to about 10 wt %, based on the total weight of the skin care composition. From a practical standpoint, these compositions will comprise the one or more alkanoyl isohexide(s) in a dermatologically acceptable carrier. Additionally, these compositions may optionally include an effective amount of one or more skin protective and/or treatment ingredients such as antioxidants, sunscreens, vitamins, anti-inflammatory agents, self-tanning agents, moisturizers, emollients, humectants, compatible solutes and the like, and mixtures thereof, in their conventional amounts.

The skin care compositions according to the present invention are generally applied topically and may take the form of a liquid, lotion, crème, serum, spray, ointment, gel, foam, liquid foundation, or balm and may be presented as a cosmetic or make-up product, antiperspirant, or another topically applicable health and beauty aid and/or pharmacological product. These types and forms of skin care compositions may themselves be in the form of emulsions, dispersions, liposomes, coacervates and the like. The skin care compositions may also take the form of various articles such as pads, swabs, wipes, sponges, and the like that are saturated with or otherwise contain or hold the actual skin care composition but which release the same or leave a film of the same when swiped across the skin surface.

The term "dermatologically acceptable carriers" refers to vehicles, diluents, and carriers known for use in dermatological compositions. These carriers are materials or combinations of materials that are used to deliver the active components, here the alkanoyl isohexide(s), to the desired application site, typically the skin. Preferred dermatologically acceptable carriers are carrier materials or compositions that are suitable for application, especially long term and repeated application, to the skin without manifesting sensitization or irritation. Generally speaking, the dermatologically acceptable carrier will comprise from about 0.1 to about 99.9% by weight of the inventive skin care compositions.

Suitable dermatologically acceptable carriers include any of the known topical excipients and like agents necessary for achieving the particular form of the skin care composition desired. Exemplary excipients include, e.g., mineral oils and emulsifying agents as well as water, alcohol, or water/alcohol combinations, or other solvent(s) or solvent systems in which the aforementioned actives may be, e.g., soluble, dispersed, emulsified, etc. Preferably, though, the skin care compositions will include excipients and the like that create a substantially stable, homogenous composition and/or provide body and viscosity to the composition so that the actives do not merely run off the skin once applied.

The specific choice of carrier or carrier ingredients will depend upon the delivery method itself as well as the speed with which the active ingredients, e.g., the alkanoyl isohexide (s), are to come in contact with or penetrate the application site. For example, an oil based carrier will remain on the skin for a relatively long period of time, allowing for a slow transfer of the active to the skin; whereas an alcohol solvent, because of its volatility, will flash off quite quickly, leaving the actives on the skin in a matter of seconds or so. Still, other solvents, like DMSO, will help speed up the penetration of the actives into the skin.

Generally speaking, any known carrier or base composition employed in traditional skin care/treatment compositions may be used in the practice of the present invention. Suitable carriers and carrier compositions are described at length in, for example, Gonzalez et. al.—U.S. Pat. No. 7,186,404; Aust et. al.—U.S. Pat. No. 7,175,834; Roseaver et. al.—U.S. Pat. No. 7,172,754; Simoulidis et. al.—U.S. Pat. No. 7,175,835; Mongiat et. al.—U.S. Pat. No. 7,101,536; Maniscalco—U.S. Pat. No. 7,078,022; Forestier et. al. U.S. Pat. No. 5,175,340, U.S. Pat. No. 5,567,418, U.S. Pat. No. 5,538,716, and U.S. Pat. No. 5,951,968; Deflandre et. al.—U.S. Pat. No. 5,670,140; Chaudhuri—U.S. Pat. No. 6,831,191, U.S. Pat. No. 6,602,515, U.S. Pat. No. 7,166,273, U.S. Pat. No. 6,936,735, and U.S. Pat. No. 6,699,463; Chaudhuri et. al.—U.S. Pat. No. 6,165,450 and U.S. Pat. No. 7,150,876; Bonda et. al. U.S. Pat. No. 6,962,692; and Wang et. al. U.S. Pat. No. 5,830,441, all of which are incorporated herein by reference in their entirety. Those skilled in the art will readily recognize and appreciate what carriers may be employed in light of the intended form and/or delivery method for the inventive sunscreen compositions.

Though a carrier by itself is sufficient, the inventive compositions of the present invention may, and preferably will, contain various other components typically associated with skin care/treatment products. For example, various skin care agents including, but not limited to, conventional skin care excipients as well as additional photoprotective agents and skin lightening agents may be present. Such agents include, but are not limited to antioxidants, sunscreens, skin lightening actives, exfoliants, anti-acne actives, vitamins, anti-inflammatory agents, self-tanning agents, moisturizers, compatible solutes, humectants, emollients and the like, and mixtures thereof, in their conventional amounts. Exemplary agents and additive materials are described briefly below as well as in the aforementioned patents, especially Maniscalco—U.S. Pat. No. 7,078,022. Each of these will be present in their conventional amount, though, as noted above and in the following examples, certain of these additives will manifest a synergy with the isohexides of the present application whereby the same performance may be realized with lesser amounts. In any event, such ingredients will typically be present in an amount of 1 to 30 wt %, preferably 2 to 20 wt %; though again, higher active ingredients, like the sunscreen actives, antioxidants, and anti-inflammatory agents may be effective at levels as low as 0.01 wt %, preferably 0.1 wt %. This is especially true for highly active agents like the meroterpenes, especially the purified versions, most especially purified bakuchiol.

Suitable antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, alkylresorcinols, meroterpenes, curcurmin and its derivatives and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, *Phyllanthus emblica, Terminalia chebula, Terminalia belerica, Phyllanthus amarus* and meroterpenes, such as, Bakuchiol (available from Sytheon Ltd under the trade name Sytenol® A) or other meroterpenes. Other examples of antioxidants may be found on pages 1612-13 of the ICI Handbook as well as in Ghosal—U.S. Pat. No. 6,124,268, both of which are incorporated herein by reference in their entirety.

Sunscreen actives are of two types, inorganic actives that work by reflecting the UV light and organic actives that work, predominately, by absorbing UV energy. The amount of the sunscreen active to be incorporated into the sunscreen formulations is that which is conventional in the art. Typically, the amount is dependent upon, among other factors, the delivery means, e.g., is it applied as a spray or lotion; the stability of the active; the efficacy of the selected sunscreen active itself; and the application rate, as well as the particular SPF desired. From the commercial perspective, another factor influencing the level of such sunscreen actives in the sunscreen formulations is the regulatory limitations on their use. In the United States, for example, strict controls are placed upon the maximum level at which approved sunscreen actives may be present. Similar regulatory/governmental controls may also dictate which sunscreen actives may be used and at what amount in other countries as well.

Suitable organic sunscreen actives include, for example, avobenzone, butyl methoxydibenzoylmethane, cinoxate, benzophenone-8, dioxybenzone, homosalate, octylsalate, menthyl anthranilate, octocrylene, ethylhexyl methoxycinnamate, octyl methoxycinnamate, octyl salicylate, oxybenzone, padimate O, ethylhexyl salicylate, benzophenone-3, p-aminobenzoic acid (PABA), ethylhexyl dimethyl PABA, glyceryl PABA, phenylbenzimidazole sulfonic acid, sulfisobezone, trolamine salicylate, 4-methylbenzylidene camphor, bisoctrizole, bemotrizinol, ecamsule, drometrizole trisiloxane, disodium phenyl dibenzimidazole tetrasulfonate, diethylamine hydroxybenzoyl hexyl bezoate, octyl triazone, hexyl benzoate, benzophenone-4, ethylhexyl triazone, diethylhexyl butamido triazone, bisimidazylate, polysilicone-15, etc.

Inorganic sunscreens include, but are not limited to, microfine surface treated titanium dioxide and microfine untreated and surface treated zinc oxide. The titanium dioxide in the sunscreen compositions preferably has a mean primary particle size of between 5 and 150 nm, preferably between 10 and 100 nm. Titanium oxide may have an anatase, rutile, or amorphous structure. The zinc oxide in the sunscreen compositions preferably has a mean primary particle size of between 5 nm and 150 nm, preferably between 10 nm and 100 nm. Examples of suitable hydrophobically modified titanium dioxide compositions include but are not limited to the following:

UV Titans® X161, M160, M262 (surface treated with stearic acid and alumina) (Kemira)
Eusolex T-2000 (surface treated with alumina and simethicone) (Merck KGaA)
T-Cote® (surface treated with dimethicone) (BASF)
Mirasun® TiW60 (surface treated with silica and alumina) (Rhodia)
Tayaca MT100T (surface treated with aluminum stearate) (Tayaca)
Tayaca MT-100SA (surface treated with silica and alumina) (Tayaca)
Tayaca MT-500SA (surface treated with silica and alumina) (Tayaca)
Tioveil® EUT, FIN, FLO, FPT, GCM, GPT, IPM, MOTG, OP, TG, TGOP (surface treated with silica and alumina, 40% dispersion in a range of cosmetic vehicle) (ICI)
Eusolex® T-45D (surface treated with alumina and simethicone, 45% dispersion in isononoylnonaoate) (Merck KGaA)
Eusolex® T-Aqua (surface treated with aluminum hydroxide, 25% dispersion in water) (Merck KGaA)

Examples of suitable untreated and hydrophobically modified zinc oxide include but are not limited to the following:
Z-Cote® (uncoated microfine zinc oxide) (BASF)
Z-Cote® HP-1 (surface treated with dimethicone) (BASF)
Sachtotec® LA 10 (surface treated with lauric acid) (Sachtleben)
Sachtotec® (uncoated microfine zinc oxide) (Sachtleben)

Spectraveil® FIN, IPM, MOTG, OP, TG, TGOP (uncoated, 60% dispersion in a range of cosmetic vehicle) (ICI)

Z-sperse® TN (untreated, dispersion in C12-15 alkyl benzoate) (Collaborative)

Z-sperse® TN (untreated, dispersion in octydodecyl neopentanoate) (Collaborative)

Most preferably, if present, the skin care compositions of the present invention will comprise a combination of such sunscreen actives. In this respect, it is well known that certain sunscreen actives have better stability, hence longevity, than others; while others have better absorptive capabilities, whether in reference to selectivity for certain UV energy of certain wavelength(s) or cumulative absorptive capabilities. Hence, by using combinations of such UV sunscreen actives, one is able to provide greater protection. Suitable combinations are well known in the art and within the skill of a typical artisan in the field.

Some sunscreens, such as avobenzone, are not photchemically stable. Therefore, it may be and is desirable to include appropriate stabilizers for improvement in sun protection. Suitable photostabilzers include, but are not limited to the following examples—Oxynex® ST (Diethylhexyl syringylidenemalonate, EMD Chemicals), RonaCare® AP (Bis-Ethylhexyl Hydroxydimethoxy Benzylmalonate, EMD Chemicals), Polycrylene® (Polyester-8, Hallstar), Solastay™ $S_1$ (Ethylhexyl methoxycrylene, Hallstar), Corapan® TQ (Diethylhexyl napthalate, Symrise), Octocrylene or combination thereof.

The skin care compositions of the present invention may also include one or more vitamins and/or their derivatives. Vitamins and vitamin derivatives include, for example, vitamin A, vitamin A propionate, vitamin A palmitate, vitamin A acetate, retinol, vitamin B, thiamine chloride hydrochloride (vitamin B.sub.1), riboflavin (vitamin B.sub.2), nicotinamide, vitamin C and derivatives (for example ascorbyl palmitate, magnesium ascorbyl phosphate, ascorbyl acetate), vitamin D, ergocalciferol (vitamin D.sub.2), vitamin E, DL-.alpha.-tocopherol, tocopherol E acetate, tocopherol hydrogensuccinate, vitamin K.sub.1, esculin (vitamin P active ingredient), thiamine (vitamin $B_1$), nicotinic acid (niacin), pyridoxine, pyridoxal, pyridoxamine, (vitamin $B_6$), pantothenic acid, biotin, folic acid and cobalamine (vitamin $B_{12}$). Preferred vitamins are, for example, vitamin A palmitate, vitamin C and derivatives thereof, DL-α-tocopherol, tocopherol E acetate, nicotinic acid, pantothenic acid and biotin. Vitamin E, which is often added to cosmetic and personal care products is also preferably stabilized by the compounds according to the invention. Additional preferred vitamins are Vitamin C and K and derivatives thereof.

The compositions of the present invention may also include one or more amino acids and their derivatives. Amino acids and their derivatives include, for example, essential and non-essential amino acids and their derivatives. Eight amino acids are generally regarded as essential for humans: phenylalanine, valine, threonine, tryptophan, isoleucine, methionine, leucine, and lysine. Additionally, cysteine (or sulphur-containing amino acids), tyrosine (or aromatic amino acids), histidine and arginine are required by infants and growing children. Essential amino acids are so called not because they are more important to life than the others, but because the body does not synthesize them, making it essential to include them in one's diet in order to obtain them. In addition, the amino acids arginine, cysteine, glycine, glutamine, histidine, proline, serine and tyrosine are considered conditionally essential, meaning they are not normally required in the diet, but must be supplied exogenously to specific populations that do not synthesize it in adequate amounts. Amino acid derivatives may be simple esters or amides or complex peptides.

Suitable emollients include those agents known for softening the skin which may be selected from hydrocarbons, fatty acids, fatty alcohols and esters. Petrolatum is a common hydrocarbon type of emollient conditioning agent. Other hydrocarbons that may be employed include alkyl benzoate, mineral oil, polyolefins such as polydecene, and paraffins, such as isohexadecane. Fatty acids and alcohols typically have from about 10 to 30 carbon atoms. Illustrative are myristic, isostearic, hydroxystearic, oleic, linoleic, ricinoleic, behenic and eruicic acids and alcohols. Oily ester emollients may be those selected from one or more of the following, triglyceride esters, acetoglyceride esters, ethoxylated glycerides, alkyl esters of fatty acids, ether esters, polyhydric alcohol esters and wax esters. Additional emollients or hydrophobic agents include $C_{12}$ to $C_{15}$ alkyl benzoate, dioctyladipate, octyl stearate, octyldodecanol, hexyl laurate, octyldodecyl neopentanoate, cyclomethicone, dicapryl ether, dimethicone, phenyl trimethicone, isopropyl myristate, capriylic/capric, triglycerides; propylene glycol dicaprylate/dicaprate and decyl oleate.

Suitable humectants include various polyhydric alcohols, especially polyalkylene glycols and, more preferably, alkylene polyols and their derivatives. Exemplary humectants include propylene glycol, dipropylene glycol, polypropylene glycol, polyethylene glycol, sorbitol, 2-pyrrolidone-5-carboxylate, hydroxypropyl sorbitol, hexylene glycol, xylitol, ethoxydiglycol 1,3-butylene glycol, 1,2,6-hexanetriol, glycerin, ethoxylated glycerin, propoxylated glycerin, compatible solutes, such as ectoin, hydroxectoin, taurines, carnithine, acetyl carnithine and mixtures thereof. When employed in effective amounts, generally from 1 to 30%, preferably from 2 to 20%, by weight of the topical composition, these additives serve as skin moisturizers as well as reduce scaling and stimulate the removal of built-up scale from the skin.

Suitable anti-inflammatory ingredients include, but are not limited to, bisabolol, curcurmin and its derivatives, retinoids, flavonoids, meroterpenes (such as Bakuchiol or its derivatives) and other polyphenolics etc. These and other anti-inflammatory agents, as well as additional anti-oxidants and the like, are disclosed in Gupta et. al. (US 2005/0048008A1) which is incorporated herein by reference in its entirety.

Examples of self-tanning ingredients include, but are not limited to, dihydroxyacetone and erythrulose.

It is to be appreciated that many of the specific ingredients mentioned above, while presented in just one or two classifications, actually manifest a plurality of properties and could rightfully be listed in two or more of the above classes. This is particularly so for the meroterpenes, especially bakuchiol, which has been shown to possess many different beneficial characteristics when applied to skin and are also shown to have gene modulation properties as well. (See Jia et. al.—US 2006/0251749A1 and Chaudhuri—US2008/0286217A1, US2009/0137534A1 and US 2009/0036545A1; all of which are hereby incorporated herein by reference in their entirety).

The present inventive composition may also include one or more skin penetrants. These are additives that, when applied to the skin, have a direct effect on the permeability of the skin barrier: increasing the speed with which and/or the amount by which certain other compounds, especially the active compounds, like the alkyl isohexides, are able to penetrate into the skin layers. Exemplary organic penetration enhancers include dimethyl sulfoxide; dimethyl isosorbide, dimethyl isomannide, diethyl isoidide, diethyl isosorbide, diethyl isomannide, isopropyl isosorbide, isopropyl isomannide, isopropyl isoidide, isopropyl myristate; decyl, undecyl or dodecyl alcohol;

propylene glycol; polyethylene glycol; $C_{9-11}$ $C_{12-13}$ or $C_{12-15}$ fatty alcohols; azone; alkyl pyrrolidones; lecithin; etc. Surfactants can also be used as penetration enhancers. Additionally, since the alkanoyl isohexides also affect cross-epidermal transport, they too may be used as skin penetration enhancers for other skin care or treatment products.

Other optional adjunct ingredients for the compositions of the present invention include preservatives, waterproofing agents, fragrances, anti-foam agents, plant extracts (Aloe vera, witch hazel, cucumber, etc), opacifiers, stabilizers, skin conditioning agents colorants, and the like, each in amounts effective to accomplish their respective functions.

The amount of the inventive composition that is to be applied to the skin is the amount that provides the desired effect of improvement in skin health and or appearance. To some extent, the amount depends upon the form of the inventive composition and its mode of application. For example, a spray formulation may be applied so as to provide a light, even coat on the skin. Lotions, creams, gels and the like are typically applied at a rate of about 0.1 to about 10 $mg/cm^2$, preferably from about 1 to about 3 $mg/cm^2$, to the skin. This rate generally provides a thin even coating on the skin surface.

The skin conditioning compositions according to the present invention may be applied to the skin for so long a necessary to address a particular problem or issue or they may be applied on a continuous basis as a matter of general skin cleansing and maintenance. Where the compositions are to be employed to address particular problems or issues, it is best to employ compositions wherein the strength or concentration of the active alkanoyl isohexide is relatively high. However, for compositions that are to be used on a continuous basis, e.g., weekly, daily, or even more frequently, a lower strength or concentration product may be suitable. In general, the desire is to attain the desired effect while minimizing the use and exposure of chemical agents.

In addition to those benefits of the inventive compositions mentioned above, it is to be appreciated that the continual, preferably daily, use of the compositions of the present invention, regardless of whether one is manifesting a problem to be addressed or not, provides a number of additional benefits to one's skin. For example, the long-term use of the inventive compositions may help with thickening the keratinous tissue (i.e., building the epidermis and/or dermis layers of the skin), thereby preventing and/or retarding atrophy of human skin; preventing and/or retarding the appearance of spider veins and/or red blotchiness on human skin; preventing and/or retarding the appearance of dark circles under the eye; preventing and/or retarding sallowness and/or sagging of human skin; soften and/or smooth lips; preventing and/or relieving itch of human skin, regulating skin texture (e.g. wrinkles and fine lines), improving skin color (e.g. redness, freckles); and the like. In essence, the long-term benefits of the continual use of the compositions of the present invention include the lessening or delayed manifestation, possibly even the prevention or repair, of skin damage owing to the natural process of skin aging as well as skin damage due to environmental factors, especially sun exposure. Generally, the use of these compositions will manifest itself in an overall improved skin quality as compared to skin which has not been treated with a composition according to the present invention, and, most especially, to which no effective product had been applied on an on-going basis

EXAMPLES

Having described the invention in general terms, Applicants now turn attention to the following examples in which specific formulations and applications thereof are evaluated. In the foregoing and in the following examples, unless otherwise indicated, all temperatures are set forth in degrees Celsius and all parts and percentages are by weight.

In the following discussion and examples the "modulating" or "regulating" of a gene refers to the ability of a compound to affect the ability of that gene to induce the production of the corresponding protein, which protein is then capable of performing at least one of its biological activities to at least some extent. In assessing performance, only those tests or samples in which at least a 150% change in gene expression was manifested were considered. Up-regulation (presented as a positive fold change) is a process which occurs within a cell triggered by a signal (originating internal or external to the cell) which results in an increased expression of one or more genes and, as a result, an increase in the protein(s) encoded by those genes. Conversely down-regulation (presented as a negative fold change) is a process resulting in decreased gene and corresponding protein expression. Up-regulation occurs for example when a cell is deficient in some kind of receptor. In this case, more receptor protein is synthesized and transported to the membrane of the cell and thus the sensitivity of the cell is brought back to normal, reestablishing homeostasis. Down-regulation occurs for example when a cell is overly stimulated by a neurotransmitter, hormone, or drug for a prolonged period of time and the expression of the receptor protein is decreased in order to protect the cell. This homeostasis can be achieved by using external agent with beneficial effects to skin.

Additionally, as used herein, the term, "p-value" is used to mean the probability that the results were not significant: for example, a p-value of 0.05 means that there are 5 chances in 100 that the results are not significant. The term "fold change" refers to the extent, as compared to the DMSO control, that the active produced an increase or decrease in gene and corresponding protein expression. A 1.5 fold increase means that 1.5 times as much of the corresponding protein was produced in those cells exposed to the active as compared to those only exposed to the DMSO control.

In performing the gene assays reported below, samples of EpiDerm tissues obtained from Mattek of Ashland, Mass., were cultured according to the manufacturer's instructions. The tissue samples were incubated in the specified test and control solutions for a period of 48 hours. Following the incubation period, the tissue samples were harvested, frozen in liquid nitrogen, and subjected to RNA extraction with a Qiagen kit. The quality of the extracted RNA was validated twice by electrophoresis and/or spectrometry (following extraction and before microarray analysis) in accordance with the methodology of Hangbao Ma et. al., Application of Real-Time Polymerase Chain Reaction (RT_PCR), The Journal of American Science, 2 (3), 2006.

Example 1

Synthesis of Alkanoyl-Isosorbide, Isomannide and Isoiodide

Example 1A

Synthesis of Dioctanoyl Isosorbide

Dioctanoyl isosorbide (DOI) was synthesized by refluxing isosorbide with 2 moles of octanoic acid in cyclohexane using p-toluene sulfonic acid as a catalyst with continuous removal of water. After completion of the reaction, DOI was purified to >98% by distillation.

Example 1B

Synthesis of Didodecanoyl Isosorbide

Didodecanoyl isosorbide was synthesized by refluxing isosorbide with 2 moles of dodecanoic acid in cyclohexane using p-toluene sulfonic acid as a catalyst with continuous removal of water. After completion of the reaction, DOI was purified to >98% by distillation.

Example 1C

Synthesis of Dihexanoyl Isosorbide

Dihexanoyl isosorbide was synthesized by refluxing isosorbide with 2 moles of hexanoic acid in cyclohexane using p-toluene sulfonic acid as a catalyst with continuous removal of water. After completion of the reaction, dihexanoyl isosorbide was purified to >98% by distillation Example 2

Gene Regulation with Dioctanoyl Isosorbide

A DNA microarray high-throughput screening of dioctanoyl isosorbide (DOI) was conducted to ascertain the applicability and suitability of employing alkanoyl isosorbides in skin conditioning applications. The test solutions of DOI were made by dissolving the DOI (>99% pure material) in DMSO at 10 mg/ml and further diluting that solution to the final concentration with type I sterile water. The gene expression assay was conducted using EpiDerm tissues incubated in the test solutions at concentration of 10 µg/ml against a 0.1% by weight DMSO control.

The test samples were hybridized and the data were analyzed using the human OneArray platform from Phalanx Biotech (Palo Alto, Calif.; www.phalanxbiotech.com). The resultant file yielded information on over 30,000 probes and was then culled to select the dermatologically relevant genes and to eliminate those results manifesting a high (greater than 0.05) predictor values and a low (less than 1.5) fold change as compared to the DMSO control. Surprisingly, DOI, whose structure is completely dissimilar to those of retinoids, alpha- or beta hydroxy acids or glycerylglycosides, was found to up-regulate CD44 and aquaporin 3 genes: an effect associated with improved skin health and appearance.

TABLE 1

| Gene Ontology | List | Up | Down | Gene set* | z-score up | z-score down |
|---|---|---|---|---|---|---|
| tissue development | 25 | 13 | 12 | 146 | 7.29 | 1.14 |
| epidermis development | 18 | 12 | 6 | 63 | 11.29 | 1.18 |
| Epidermis morphogenesis | 9 | 7 | 2 | 22 | 11.48 | 0.61 |
| Epidermal cell differentiation | 8 | 7 | 1 | 19 | 12.43 | −0.14 |
| Keratinization | 8 | 7 | 1 | 16 | 13.64 | 0.04 |
| keratinocyte differentiation | 5 | 2 | 3 | 18 | 3.28 | 1.9 |
| epidermal growth factor receptor signaling pathway | 3 | 1 | 2 | 10 | 2.16 | 1.86 |
| positive regulation of angiogenesis | 2 | 1 | 1 | 7 | 2.72 | 0.92 |
| keratinocyte proliferation | 2 | 1 | 1 | 4 | 3.78 | 1.6 |

TABLE 1-continued

| Gene Ontology | List | Up | Down | Gene set* | z-score up | z-score down |
|---|---|---|---|---|---|---|
| positive regulation of keratinocyte migration | 1 | 1 | 0 | 2 | 5.53 | −0.36 |
| positive regulation vascular endothelial growth factor production | 1 | 1 | 0 | 2 | 5.53 | −0.36 |

*For more detailed information of gene set analysis see D Nam and S Y Kim, "Gene-set Approach for Expression Pattern Analysis', Briefings in Bioinformatics, 9(3): 189-197, 2007.

Specifically, the Gene Ontology analysis showed two types of skin-relevant responses elicited by DOI. The first one, summarized in Table 1, consists of an overall stimulatory effect on epidermis morphogenesis, through the stimulation of proliferation, migration and differentiation of keratinocytes, accompanied by an increase in angiogenesis. It is interesting to note that this epidermis-stimulatory effect has been observed against a generally conservative background of suppressed gene expression and signal transduction. As evident from Table 2, this data points to the specificity of the stimulatory effect of DOI towards the skin tissue, while maintaining the overall systemic homeostasis. Also, as evident from Table 3, exposure to DOI manifested an activation of some selective components of the immune response, which activation failed to translate into or manifest a chronic inflammatory response.

TABLE 2

| Gene Ontology | List | Up | Down | Gene set | z-score up | z-score down |
|---|---|---|---|---|---|---|
| Signal transduction | 84 | 15 | 69 | 843 | 0.58 | 2.98 |
| Gene expression | 78 | 8 | 70 | 1085 | −2.57 | 0.71 |
| negative regulation of cell proliferation | 10 | 4 | 6 | 86 | 2.34 | 0.38 |
| transmembrane receptor protein tyrosine kinase signaling pathway | 15 | 2 | 13 | 69 | 0.9 | 4.52 |
| negative regulation of cell proliferation | 10 | 4 | 6 | 86 | 2.34 | 0.38 |
| homeostatic process | 24 | 13 | 11 | 173 | 2.01 | −1.49 |
| Ion homeostasis | 8 | 4 | 4 | 75 | 2.66 | −0.25 |
| chemical homeostasis | 10 | 4 | 6 | 92 | 2.18 | 0.21 |
| calcium ion homeostasis | 4 | 2 | 2 | 29 | 2.33 | 0.2 |
| cellular calcium ion homeostasis | 4 | 2 | 2 | 29 | 2.33 | 0.2 |
| cellular metal ion homeostasis | 4 | 2 | 2 | 31 | 2.21 | 0.1 |
| Potassium ion homeostasis | 1 | 1 | 0 | 2 | 5.53 | −0.36 |
| temperature homeostasis | 1 | 1 | 0 | 3 | 4.44 | −0.44 |
| cellular homeostasis | 17 | 10 | 7 | 102 | 2.67 | −0.96 |

The DOI assay was also inclusive of those genes commonly considered important for improving hydration of the dermis and epidermis, regulating both epidermal differentiation and lipid synthesis/secretion, which in turn influence permeability barrier homeostasis. Tables 4, 5 and 6 show the DNA microarray values of those genes which manifested at least a 150% modulation by DOI as compared to the Control. Of interest is the modulation of those genes involved in aquaporin, the detoxifying enzymes, the tight junction (i.e., those involved in cell-cell junctions (tight junctions)), desmosomes and epidermal differentiation.

TABLE 3

| Gene Ontology | List | Up | Down | Gene set | z-score up | z-score down |
|---|---|---|---|---|---|---|
| immune response | 15 | 6 | 9 | 148 | 2.49 | 0.03 |
| Fever | 1 | 1 | 0 | 2 | 5.53 | −0.36 |
| negative regulation of immune response | 1 | 0 | 1 | 2 | −0.18 | 2.62 |
| positive regulation of cytokine secretion | 1 | 1 | 0 | 5 | 3.33 | −0.57 |
| positive regulation of interleukin-2 biosynthetic process | 1 | 1 | 0 | 4 | 3.78 | −0.51 |
| positive regulation of interleukin-6 biosynthetic process | 1 | 0 | 1 | 2 | −0.18 | 2.62 |
| Regulation of macrophage activation | 1 | 0 | 1 | 2 | −0.18 | 2.62 |
| response to cytokine stimulus | 2 | 1 | 1 | 11 | 2.02 | 0.43 |
| chronic inflammatory response | 1 | 0 | 1 | 2 | −0.18 | 2.62 |

TABLE 4

Modulation of Genes associated with water homeostasis, detoxification and barrier function by DOI

| Genes | Gene Description | Functions | % Control |
|---|---|---|---|
| CD44 | Hyaluronoglucosaminidase1 | Water homeostasis | 309 |
| GSTM3 | Glutathione S-transferase Mu3 | Detoxification | 158 |
| GSTM5 | Glutathione S-transferase Mu5 | Detoxification | 179 |
| CLDN4 | Claudin-4 (tight junction) | Barrier function | 316 |
| AQP3 | Aquaporin 3 | Water homeostasis | 340 |
| TJP1 | Tight junction protein ZO-1 | Barrier function | 181 |
| TJP2 | Tight junction protein ZO-2 | Barrier function | 542 |
| JAM-1 | Junctional adhesion molecule 1 | Barrier function | 158 |

TABLE 5

Modulation of genes associated with Desmosomes by DOI

| Gene | Gene Description | Function | % Control |
|---|---|---|---|
| DSG3 | Desmoglein 3 | Mediates adhesion to desmosome | 259 |
| DSC2 | Desmocollin 2 | Mediates adhesion to desmosome | 420 |
| JUP | Junction Plakoglobin (γ catenin) | Essential for the formation & stabilization of desmosomal plaque | 312 |
| PKP1 | Plakophilin 1 | Essential for the formation & stabilization of desmosomal plaque | 166 |
| DSP | Desmoplakin | Mediates linkage to the cytoskeleton | 167 |
| CDH1 | E Cadherin | Controls keratinocytes and desmosomal adhesion | 496 |

TABLE 6

Modulation of genes associated with epidermal differentiation by DOI

| Gene | Gene Description | Function | % Control |
|---|---|---|---|
| IVL | Involucrin | Cross-linking with envoplakin & periplakin | 153 |
| SPPR3 | Small proline-rich protein 3 | Subsequent inclusion in the envelope | 332 |

TABLE 6-continued

Modulation of genes associated with epidermal differentiation by DOI

| Gene | Gene Description | Function | % Control |
|---|---|---|---|
| K5 | Keratin 5 | Involved in epidermal differentiation in basal layer | 166 |
| K10 | Keratin 10 | Involved in epidermal differentiation in granular layer | 166 |
| LCE1E | Late cornified envelope protein 1E | Essential for maintenance of barrier function | 203 |
| LCE3A | Late cornified envelope protein 3A | Essential for maintenance of barrier function | 263 |
| LCE3B* | Late cornified envelope protein 3B | Essential for maintenance of barrier function | 291 |
| LCE3C* | Late cornified envelope protein 3C | Essential for maintenance of barrier function | 558 |
| LCE3D | Late cornified envelope protein 3D | Essential for maintenance of barrier function | 354 |

*Lack of these two genes found in psoriatic & atopic dermatitis patients;
Reference: Nature Genetics 41, 211-215 (2009)

Taken together, the data indicates that DOI is bioactive in the EpiDermFT model. The major activities are stimulation of epidermal morphogenesis, select components of the immune response, and detoxifying enzymes. DOI also has an effect on cell-cell junctions and extracellular matrix, which is possibly related to facilitating migration of keratinocytes.

Example 3

Real-time Polymerase Chain Reaction (rtPCR) with DOI

As in Example 2, gene expression analyses using DNA microarrays were conducted on samples of EpiDermFT tissues (cat # EFT412) which had been incubated in a DOI test solution of 50 ug/ml concentration and compared to similar tissue samples incubated in Sterile type I water and 0.1% DMSO as controls. A two-step RT-PCR analysis was conducted on the following genes:

```
Homo CD44-F
Homo CD44-R
Homo Aquaporin 3-F
Homo Aquaporin 3-R
Homo ZO-2 F
Homo ZO-2 R
Homo Claudin 4-F
Homo Claudin 4-R
```

RT-PCR analysis was conducted at Phalanx Biomed (Palo Alto, Calif.) for 120 min at 37° C. with High Capacity cDNA Reverse Transcription Kit according to the standard protocol of the supplier (Applied Biosystems). Quantitative PCR was performed by the condition: 10 min at 95° C., and 40 cycles of 15 sec at 95° C., 1 min at 60° C. using 2× Power SYBR Green PCR Master Mix (Applied Biosystems) and 200 nM of forward and reverse primers. Each assay was run on an Applied Biosystems 7300 Real-Time PCR system in triplicate and expression fold-changes were derived using the comparative $C_T$ method.

As evident from the results presented in Table 7, relative quantification, with GAPDH as the endogenous control, using the comparative $C_T$ method shows that EpiDerm samples incubated with DOI are enriched in Aquaporin-3, Claudin-4 and ZO-2 transcripts. These results are in agreement with the results previously obtained using the DNA microarray hybridization technique as shown in Example 2. In contrast, DOI does not seem to modulate the transcription of the CD-44 gene.

TABLE 7

| Product | Aquaporin 3 | Claudin 4 | ZO-2 | CD44 |
|---|---|---|---|---|
| DOI (fold change vs. control) | 2.83 | 2.54 | 1.66 | −1.07 |
| Control | 1.00 | 1.00 | 1.00 | 1.00 |

Example 4

Skin Sensitivity Study with Synovea® DOI

Given the known sensitivity issues associated with retinoids and hydroxyl acids, evaluation of the skin sensitivity to DOI was also evaluated. Skin sensitivity was evaluated following the method cited in the reference *Appraisal of the Safety of Chemicals in Food, Drugs and Cosmetics*, published by The Association of Food and Drug Officials of The United States. The method employs nine inductive patching and not the ten cited in the reference under occlusive patch conditions.

Samples were prepared for evaluation by diluting DOI in corn oil to a 5% concentration, with dilutions freshly prepared on each application day. 0.2 ml or 0.2 g of the diluted test material was dispensed onto an occlusive, hypoallergenic patch and the treated patch applied directly to the skin of the infrascapular regions of the back, to the right or left of the midline of each subject: one hundred and eleven subjects were employed. After application of the patch, each subject was dismissed with instructions not to wet or expose the test area to direct sunlight. The patch was removed by the subject after 24 hours. This procedure was repeated every Monday, Wednesday and Friday for three consecutive weeks until a series of nine consecutive 24 hour exposures had been made. During the test period, the test area on the subjects' backs were observed for evidence of edema or erythema just before applications two through nine and the next test date following application nine. If evidence of a reaction was found, the area of edema and/or erythema was then measured and recorded: edema being estimated by an evaluation of the skin with respect to the contour of the unaffected normal skin. The subjects were then given a 10-14 day rest period after which a challenge or retest dose was applied once to a previously unexposed test site. The retest dose was equivalent to any one of the original nine exposures. Reactions were scored 24 and 48 hours after application. Based on the test results, the 5% dilution in corn oil of DOI was determined to be a NON-PRIMARY IRRITANT and a NON-PRIMARY SENSITIZER according to the reference.

Examples 5A-5D

Formulations for Topical Applications

The following tables set forth various formulations and embodiments of compositions according to the present invention. Following each table is a brief description of the process by which each formulation is made.

Example 5A

Lotion with 2% Dioctanoyl Isosorbide

| INCI Name | Trade Name/Supplier | % w/w |
|---|---|---|
| Phase A-1 | | |
| Deionized water | | 80.70 |
| Disodium EDTA | Versene Na/Dow | 0.10 |
| Phase A-2 | | |
| Xanthan Gum | Vanzan NF/Vanderbilt | 0.20 |
| Phase B | | |
| Caprylic/Capric Triglyceride | Myritol 318/Cognis | 6.00 |
| Squalane | Fitoderm/Centerchem | 1.00 |
| Cetyl Esters | Crodamol SS/Croda | 1.00 |
| Cetyl Alcohol | Crodacol C-70/Croda | 1.00 |
| Dimethicone | Dow Corning 200,50 cst/ Dow Corning | 2.00 |
| Glyceryl Stearate, PEG-100 Stearate | Arlacel 165/Uniqema | 3.50 |
| Dioctanoyl Isosorbide | Synovea ® DOI/Sytheon | 2.00 |
| Phase C | | |
| Hydroxyethyl Acrylate/Sodium Acryloyldimethyl Taurate Copolymer & Squalane & Polysorbate 60 | Simulgel NS/Seppic | 1.50 |
| Phase D | | |
| Phenoxyethanol, Methylparaben, propylparaben, Ethylparaben | Phenonip XB.Clariant | 1.00 |
| Total | | 100.00 |

Procedure:
Combine the ingredients of Phase A-1; disperse Phase A2 in Phase A1 while stirring and heat the combined Phase A-1/A-2 to 75° C. Combine the ingredients of Phase B and heat to 75° C. Add Phase B to Phase A with good mixing. Homogenize the mixture at moderate speed, while adding Phases C and D. Cool the batch with propeller agitation until the mixture is homogeneous.

Example 5B

Anti-acne Lotion with 2% DOI, 1% Bakuchiol and 2% Salicylic acid

| INCI Name | Trade Name/Supplier | % W/W |
|---|---|---|
| Phase A | | |
| Deionized water | | 63.25 |
| Disodium EDTA | TiTriplex/Merck KGaA | 0.10 |
| Propylene Glycol | Propylene Glycol/Lyondel | 2.00 |
| Sorbitol | Sorbo (70% soln.)/Uniqema | 2.00 |
| Sodium Lauryl Sulfate | Stepanol ME-Dry/Stepan | 0.15 |
| Phase B | | |
| Glyceryl Stearate | Tegin M/Goldschmidt | 5.00 |
| Stearic acid | Emersol 132/Cognis | 1.00 |
| Persea Gratissima (Avocado) oil Unsaponifiables | Crodarom Avocadin/Croda | 14.00 |

-continued

| INCI Name | Trade Name/Supplier | % W/W |
|---|---|---|
| Dioctanoyl Isosorbide | Synovea ® DOI/Sytheon | 1.00 |
| Beeswax | White Bleached NF Beeswax Prills/Ross | 1.50 |
| Bakuchiol | Sytenol ® A/Sytheon | 1.00 |
| Phase C | | |
| Salicylic acid | | 2.00 |
| Pentylene Glycol | Hydrolite-5/Symrise | 3.00 |
| Dimethyl Isosorbide | Arlasolve DMI/Uniqema | 3.00 |
| Phase D | | |
| Propylene glycol, DMDM Hydantoin, Methylparaben | Paragon/McIntyre | 1.00 |
| Total | | 100.00 |

Procedure:

The components of each of Phase A and Phase B are separately combined and heated to 70-75° C. Phase A is then added to Phase B while stirring. After mixing well, Phase A/B is homogenized and allowed it to reach ~40° C. The Phase C components are mixed with slight warming ~40° C. and then added to Phase A/B. The pH is adjusted with triethanolamine to ~4.5. Thereafter, Phase D is added while stirring until a uniform composition is achieved.

Example 5C

Sunscreen Lotion with DOI

| INCI Name | Trade Name/Supplier | % W/W |
|---|---|---|
| Phase A-1 | | |
| Deionized water | | 66.95 |
| Disodium EDTA | TiTriplex/Merck KGaA | 0.10 |
| Propylene Glycol | Propylene Glycol/Lyondell | 3.00 |
| Glycerol | Emery 916/Cognis | 2.00 |
| Phase A-2 | | |
| Acrylates/C-10-30 Alkyl Acrylate Crosspolymer | Carbopol EDT 2020/Noveon | 0.15 |
| Xanthan gum | Vanzan NF/Vanderbilt | 0.15 |
| Phase B | | |
| Cetyl Alcohol, Glyceryl Stearate, PEG-75, Ceteth-20 and Steareth-20 | Emollium Delta/Gattefosse | 4.00 |
| Dimethicone | DC 200 Fluid/Dow Corning | 0.50 |
| C30-36 Olefin/Isopropyl maleate/MA Copolymer | Performa V1608/New Phase Technologies | 1.00 |
| C12-15 Alkyl Benzoate | Finsolv TN/Finetex | 7.00 |
| Dioctanoyl Isosorbide | Synovea ® DOI/Sytheon | 3.00 |
| Butyl Methoxydibenzoylmethane | Eusolex 9020/EMD Chemicals | 2.00 |
| Diethylhexyl Syringylidene Malonate, Caprylic/Capric Triglycerides | Oxynex ST/EMD Chemicals | 1.00 |
| Homosalate | Eusolex HMS/EMD Chemicals | 8.00 |
| Phase C | | |
| Triethanolamine | TEA 99%/Union Carbide | 0.15 |
| Phase D | | |
| Phenoxyethanol and Isopropylparaben and isobutylparaben and butylparaben | Liquapar | 1.00 |
| Total | | 100.00 |

Procedure:

Disperse Phase A-2 in Phase A-1 with agitation and heat to 75 C. Combine Phase B and heat to 75 C. Add Phase B to Phase A-1/A-2 with continuous stirring. Homogenize the mixture for 2-3 minutes, and cool the batch to 45 C. Add Phases C and D; and mix until uniform.

Example 6

Clinical Studies

A clinical study was conducted over a 21 day period involving thirty women divided into two groups of fifteen. Four lotions were evaluated, two different lotions on each group of fifteen. The four lotions were as follows: DOIG (a mixture containing Synovea® DOI (2%)+Glycerol (2%)), DOI (Synovea® DOI (2%)), G (Glycerol (2%)) or P (a placebo containing neither DOI nor Glycerol): the formulations for which are presented in Table 8.

TABLE 8

Products used for clinical studies

| INCI Name | Trade Name/Supplier | % W/W | | | |
|---|---|---|---|---|---|
| | | P | G | DOI | DOIG |
| Phase A | | | | | |
| Deionized water | | 86.5 | 84.5 | 84.5 | 82.5 |
| Disodium EDTA | TiTriplex/Merck KGaA | 0.10 | 0.10 | 0.10 | 0.10 |
| Glycerol | | — | 2.00 | — | 2.00 |
| Phase B | | | | | |
| Caprylic/Capric Triglycerides | Myritol 312/Protachem CTG | 6.00 | 6.00 | 6.00 | 6.00 |
| Glyceryl Stearate (and) PEG-100 Stearate | Arlacel 165/Stepan GMS SE/AS | 3.5 | 3.5 | 3.5 | 3.5 |
| Cetyl Alcohol NF | Cetyl Alcohol | 1.00 | 1.00 | 1.00 | 1.00 |
| Dimethicone | Dimethicone, 50 cs/Dow Corning | 2.00 | 2.00 | 2.00 | 2.00 |
| Dioctanoyl Isosorbide | Synovea ® DOI/Sytheon | — | — | 2.00 | 2.00 |

TABLE 8-continued

Products used for clinical studies

| INCI Name | Trade Name/ Supplier | % W/W | | | |
|---|---|---|---|---|---|
| | | P | G | DOI | DOIG |
| Sodium Acrylate/Acryloyldimethyl Taurate Copolymer (and) Squalene (and) Polysorbate | Simugel NS/Seppic | 2.00 | 2.00 | 2.00 | 2.00 |
| Phase C | | | | | |
| Phenoxyethanol/Caprylyl Glycol | Optiphen/ Microcare PHG | 1.00 | 1.00 | 1.00 | 1.00 |
| Total | | 100 | 100 | 100 | 100 |

The clinical test formulations were prepared as follows: Combine Phase A ingredients with mixing and heat to 70 C. Combine Phase B and heat to 70 C. Add Phase B to Phase A with continuous stirring. Homogenize the mixture for 2-3 minutes, and cool the batch to 45 C. Add Phases C and mix until uniform.

As noted, the test volunteers were grouped into two groups of fifteen. The first group evaluated the DOI versus the P whereas the second group evaluated the DOIG versus the state of the art G. Each lotion was generously applied to the volar arm, one lotion to the left and the other to the right, twice a day for 14 days followed by a washout period. An untreated test area was identified on each upper arm, above the volar region, as a further control to account for environmental and health related factors. Each treated and untreated area was evaluated prior to the first application of the lotion (the baseline) and again on the $14^{th}$, $16^{th}$ $18^{th}$ and $21^{st}$ day from the first application of the test lotions to assess moisture content using Nova Meter (International Flora Technologies, Ltd.).

TABLE 9

Improvement in skin hydration with products vs. placebo

| Products | 14 days | | 16 days | | 18 days | | 21 days | |
|---|---|---|---|---|---|---|---|---|
| | UT | BL | UT | BL | UT | BL | UT | BL |
| DOIG | 33% | 34% | 30% | 29% | 21% | 21% | 12% | 11% |
| DOI | 12% | 12% | 10% | 10% | 7% | 7% | 5% | 5% |
| G | 19% | 19% | 13% | 14% | 7% | 7% | 5% | 4% |
| Placebo | 1% | 1% | 1% | 1% | 1% | 1% | 1% | 1% |

The results, presenting the percent (%) change in skin hydration from the baseline ("BL") as well as from the untreated area ("UT") at the time of testing are presented in Table 9. When compared to baseline (pre-application), sample DOIG demonstrated 34% improvement in hydration of the skin at two weeks. With the cessation of the treatment, a loss of hydration was noted as the skin began to revert to its pretreatment hydration. The improvement in hydration, as compared to the baseline was 29%, 21% and 11% on the $2^{nd}$, $4^{th}$ and $7^{th}$ day following cessation of treatment, respectively. When used alone, the DOI and the glycerol, the latter a known skin moisturizing agent, both provided a marked improvement of skin hydration, though that offered by the glycerol was initially higher, the rate of loss of hydration following cessation of application was lower with the DOI. Finally, the placebo provided negligible skin hydration, indicating that the contribution to the improvement of the actives is likewise negligible. As also noted in Table 6, essentially the same results were obtained in comparing the treated versus untreated areas indicating that neither environmental nor health factors played any role in the results. In all cases, the statistical significance of these results based on t-Test value is 0.00 with a % confidence of 100%.

This human clinical study clearly shows the effectiveness of DOI by itself as well as the synergy in performance by combining the DOI with the traditional moisturizing agent, glycerol.

Without further elaboration, it is believed that one skilled in the art, using the preceding description, can utilize the present invention to its fullest extent. Furthermore, while the present invention has been described with respect to aforementioned specific embodiments and examples, it should be appreciated that other embodiments, changes and modifications utilizing the concept of the present invention are possible, and within the skill of one in the art, without departing from the spirit and scope of the invention. The preceding preferred specific embodiments are, therefore, to be construed as merely illustrative, and not limitative of the remainder of the disclosure in any way whatsoever.

I claim:

1. A method of ameliorating and/or treating diseases affecting skin hydration and barrier homeostasis, selected from the group consisting of eczema, psoriasis, hereditary ichthyosis, and atopic dermatitis, comprising applying to those areas of the skin afflicted with such conditions or diseases a remedially effective amount of a topical composition comprising at least one monoalkyl-, dialkyl-, monoalkanoyl- or dialkanoyl-isohexide having the general formula (I) or (II):

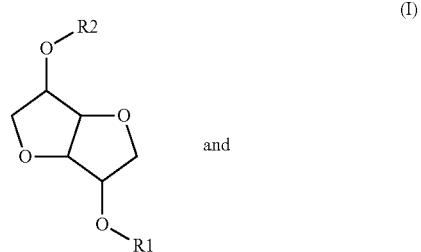

(I)

and (II)

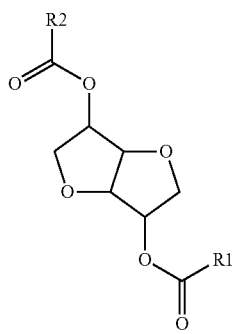

wherein $R_1$ and $R_2$, which may be the same or different, are independently selected from straight chain or branched; saturated or unsaturated alkyl groups having from 4 to 30 carbon atoms, said carbon number including the carbonyl carbon atom in the case of structure (II), provided that when $R_1$ and $R_2$ are different, one of $R_1$ or $R_2$ may also be hydrogen or a straight chain or branched; saturated or unsaturated alkyl group of from 1 to 4 carbon atoms.

2. The method of claim 1 wherein the composition is a liquid and is applied as a spray in a light even coat to the skin or is a lotion, cream, gel or other semi-solid composition that is applied at a rate of from about 0.1 to about 10 mg/cm$^2$ least once a day for an extended period of time or for a period long enough to manifest an improvement in the skin condition for which it was applied.

3. The method of claim 1 wherein at least one $R_1$ and $R_2$ is of from 6 to 22 carbon atoms, including the carbonyl atom in the case of structure (II); provided that when $R_1$ and $R_2$ are different, one of $R_1$ or $R_2$ may also be hydrogen or a straight chain or branched; saturated or unsaturated alkyl group of from 1 to 3 carbon atoms.

4. The method of claim 1 wherein at least one $R_1$ and $R_2$ is of from 8 to 18 carbon atoms.

5. The method of claim 1 wherein the isohexide comprises one or more ethers according to structure (I).

6. The method of claim 1 wherein the isohexide comprises one or more esters according to structure (II).

7. The method of claim 1 wherein the isohexide is dioctanoyl isohexide.

8. The method of claim 1 wherein the composition comprises from 0.1 to 99.9 wt. % of the one or more isohexides and from 99.9 to 0.1 wt. % of a suitable carrier.

9. The method of claim 1 wherein the isohexide is present in an amount of from about 0.5 to about 30 wt. % based on the total weight of the composition.

10. The method of claim 1 wherein the isohexide is present in an amount of from about 1.0 to about 10 wt. %, based on the total weight of the composition.

11. The method of claim 1 wherein the composition further comprises an effective amount of one or more skin protective or treatment ingredients including antioxidants, sunscreens, skin lightening actives, exfoliants, anti-acne actives, vitamins, anti-inflammatory agents, self-tanning agents, moisturizers, emollients, humectants, compatible solutes, and mixtures thereof.

12. The method of claim 1 wherein the composition further comprises from 0.01 to 30 wt. % of a meroterpene, from 1 to 30 wt. % of glycerol, or both.

13. The method of claim 12 wherein the meroterpene is bakuchiol.

14. The method of claim 1 wherein the disease is one which adversely affects the production of Aquaporin 3.

15. The method of claim 1 wherein the disease is one which adversely affects the production of Hyaluronoglucosaminidase.

16. The method of claim 1 wherein the disease is associated with a lack of late cornified envelope protein 3B, late cornified envelope protein 3C or both.

17. The method of claim 1 wherein the composition further comprises glycerol.

18. The method of claim 7 wherein composition further comprises glycerol.

* * * * *